(12) United States Patent
Götz et al.

(10) Patent No.: US 6,600,071 B2
(45) Date of Patent: Jul. 29, 2003

(54) METHOD FOR PRODUCING 1-SUBSTITUTED 5-HYDROXPYRAZOLES

(75) Inventors: Norbert Götz, Worms (DE); Roland Götz, Neulussheim (DE); Michael Rack, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 26 days.

(21) Appl. No.: 10/228,373

(22) Filed: Aug. 27, 2002

(65) Prior Publication Data

US 2003/0109717 A1 Jun. 12, 2003

Related U.S. Application Data

(62) Division of application No. 09/830,350, filed as application No. PCT/EP99/08275 on Oct. 30, 1999, now Pat. No. 6,472,538.

(30) Foreign Application Priority Data

Nov. 5, 1998 (DE) .......................... 198 51 100
Mar. 10, 1999 (DE) .......................... 199 10 505

(51) Int. Cl.$^7$ .......................... C07C 243/30
(52) U.S. Cl. .......................... 564/151; 548/366.1
(58) Field of Search .......................... 564/151

(56) References Cited

U.S. PATENT DOCUMENTS

| 4,323,705 A | * | 4/1982 | Knorr .......................... 564/151 |
| 4,643,757 A | | 2/1987 | Baba et al. |
| 4,744,815 A | | 5/1988 | Baba et al. |
| 4,812,593 A | | 3/1989 | Hoelderich et al. |
| 4,931,565 A | | 6/1990 | Baba et al. |
| 5,510,512 A | | 4/1996 | Strutz |
| 5,631,210 A | | 5/1997 | Tseng |

FOREIGN PATENT DOCUMENTS

| DE | 3641 605 | 6/1988 |
| DE | 158 462 | 5/1990 |
| JP | 5 8140 073 | 8/1983 |
| JP | 5 8140 074 | 8/1983 |
| JP | 5 8174 369 | 10/1983 |
| JP | 6 0051 175 | 3/1985 |
| JP | 6 0156 643 | 8/1985 |
| JP | 6 1189 271 | 8/1986 |
| JP | 6 1229 852 | 10/1986 |
| JP | 03044375 | 2/1991 |
| JP | 06166666 | 6/1994 |
| JP | 6168659 | 6/1994 |
| WO | WO 96/25412 | 8/1996 |
| WO | WO 96/30368 | 10/1996 |
| WO | WO 96/31507 | 10/1996 |
| WO | WO 97/01550 | 1/1997 |
| WO | WO 97/08164 | 3/1997 |
| WO | WO 97/12885 | 4/1997 |
| WO | WO 97/19087 | 5/1997 |
| WO | WO 97/23135 | 7/1997 |
| ZA | 9510980 | 12/1995 |

OTHER PUBLICATIONS

Dorn et al. "Alkylierung 1–acylieter Pyrazolidone—(3) une Synthesen 2–substituierter Pyrazolidone—(3) sowie 1–substituierter 5–Hydroxy–pyrazole" Journal für praktische Chemie, vol. 313 (1971) pp. 115–128.

Dorn et al. "die Synthese von 3(5)–Hydrosyl–pyrazol sowie von 5–Hydroxy–1–methyl–und 5–Hydroxy–1–cyclohexyl–pyrazol" Journal für praktische Chemie, vol. 313 (1971) pp. 1118–1124.

Lingens et al. "Über die Unsetzung Narürlich Vorkommender Pyrimidinbasen Mit Hydrazin Und Methylsubstituierten Hydrazinen" Annalen vol. 686 (1965) pp. 134–145.

Sucrow et al. "Einige Produkte aus 1–Alkyl–5–hydroxy–3–pyrazolcarbonsäuer–methylestern" Chem Ber vol. 109 (1976) pp. 261–267.

Quang et al. "Preparation Simple ET Stereoselective C' Alkoxy–3 Propenals E" Tetrahedron Letters, vol. 24, No. 47 (1983) pp. 5209–5210.

Ireland et al. "Enolate Claisen Rearrangement of Esters from Furanoid and Pyranoid Glycals" J. Org. Chem. vol. 45 (1980) pp. 48–61.

(List continued on next page.)

Primary Examiner—Robert W. Ramsuer
(74) Attorney, Agent, or Firm—Keil & Weinkauf

(57) ABSTRACT

A process for preparing compounds of the formula I

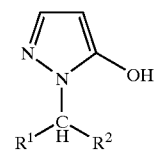

I in which $R^1$ is hydrogen, an aliphatic group having 1–8 carbon atoms, $C_1$–$C_6$-alkoxycarbonyl, $C_1$–$C_6$-alkylthiocarbonyl or a cyclic ring system having 3–14 ring atoms, and $R^2$ is hydrogen, an aliphatic group having 1–8 carbon atoms, or $R^1$ and $R^2$ together with the carbon atom to which they are bound form a cyclic or bicyclic ring system having 3–14 ring atoms, comprises the preparation of compounds of the formula II

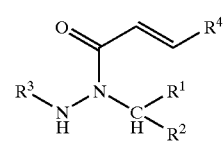

II in which $R^3$ and $R^4$ are readily detachable groups and $R^1$ and $R^2$ are as defined above, as starting materials or intermediates and the cyclization of these under suitable reaction conditions to give compounds of the formula I. The intermediates of the formula II are novel.

12 Claims, No Drawings

OTHER PUBLICATIONS

Winterfeld et al. "Der sterische Verlauf von Additionen an die Driefachbindung" Chem. Ber. vol. 99 (1996) pp. 450–459.

Kataoaka et al. "Stereoselective Addition of Alcohol to Acetylenecarboxylate Catalyzed by Silver (l) Salt" Chemistry Letters (1996) pp. 727–728.

Lapkin et al. "Dichloromethyl Alkyl Ethers and Sulfides in the Reformatskii Reaction" Zhurnal Oranicheskoi Khimii vol. 22 No. 4 (1986) pp. 738–743.

Torii et al. "A Practical Access to Methyl 3,3–Diemethoxypropionates, N–Protected β–Aminoacarylates, and β–Aminoacrylonitrile Using an Electrochemical Procedure" J. Org. Chem. vol. 50, (1985) pp. 4157–4160.

Tietze et al. "Highly Efficient Syntheses of Alkyl 3,3–Dialkoxyproponates, Alkyl 4–Ethoxy–2–oxo–3–butenoates and Monoprotected Manlonaldehydes" Synthesis vol. 4 (1988) pp. 274–277.

K. Kirschke "1H–Pyrazole" Hetarene III (1994) pp. 459–464.

* cited by examiner

METHOD FOR PRODUCING 1-SUBSTITUTED 5-HYDROXPYRAZOLES

This is a divisional application of U.S. Ser. No. 09/830,350, which was filed as PCT/EP 99/08275 on Oct. 30, 1999 now U.S. Pat. No. 6,472,538.

The present invention relates to a process for preparing substituted hydroxypyrazoles, and also to novel intermediates.

Lower 1-alkyl-5-hydroxypyrazoles are known compounds which are used as intermediates for active compounds in agrochemicals, in particular for preparing herbicides (see WO 97/23135, WO 97/19087, U.S. Pat. No. 5,631,210, WO 97/12885, WO 97/08164, ZA 9510980A, WO 97/01550, WO 96/31507, WO 96/30368, WO 96/25412).

As processes for preparing lower 1-alkyl-5-hydroxypyrazoles the following syntheses are known:

1. A preparation in which 2-methyl-1-(p-toluenesulfonyl)-3-pyrazolidone or 2-methyl-1-acetylpyrazolidone is hydrolyzed (J. Prakt. Chem. 1971, 313, 115–128 and J. Prakt. Chem. 1971, 313, 1118–1124);
2. A variant in which an alkyl ester of 5-hydroxy-1-alkylpyrazole-4-carboxylic acid is built up by cyclizing a dialkyl alkoxymethylenemalonate using lower alkylhydrazines, subsequently adding an aqueous mineral acid solution to this reaction product and carrying out the hydrolysis and decarboxylation simultaneously (see JP 61257974, JP 60051175, JP 58174369, JP 58140073 and JP 58140074 and also U.S. Pat. No. 4643757);
3. A synthesis in which ethyl propiolate is reacted with methylhydrazine to form 5-hydroxy-1-methylpyrazole (Annalen 1965, 686, 134–144);
4. A synthetic route in which,3-hydrazinopropionic esters formed by addition of hydrazine onto acrylic esters are reacted with aldehydes to give the corresponding hydrazones and are subsequently cyclized (see JP 06166666, JP 61229852 and JP 61268659 and also EP 240001);
5. A synthetic variant in which 5-hydroxy-1-methylpyrazole-3-carboxylic acid is dissociated thermally (Chem. Ber. 1976, 109, p. 261).;
6. A process in which 3-alkoxyacrylic esters are reacted with methylhydrazine to give 1-methyl-5-hydroxypyrazole (see JP 189 271/86).

The above-described syntheses have various disadvantages:

In the 1st synthetic route mentioned above, the process has a plurality of stages and is complicated. The insertion and removal of a protective group is cumbersome, results in additional steps and reduces the yield.

The 2nd method of preparation has a plurality of stages and, in addition, forms not only the 1-alkyl-5-hydroxypyrazoles but at the same time also the regioisomeric 1-alkyl-3-hydroxypyrazoles which have to be separated from the target compounds at some cost. Furthermore, the synthesis gives a poor C yield since use is made of a C4 building block from which a C atom has to be removed again at the end of the process.

In the 3rd synthetic variant, which describes only the preparation of 1-methyl-5-hydroxypyrazole, the use of amounts of methylhydrazine far above the stoichiometric amount is indispensable, thus making the process uneconomical. In addition, the 3-hydroxy-1-methylpyrazole which is likewise formed has to be removed at some cost from the 1-methyl-5-hydroxypyrazole during the purification. Furthermore, this process is uneconomical because of the high price of the propiolic ester.

In the 4th alternative, the process has a plurality of stages and is complicated. The last step of the complicated process gives only poor yields and many by-products.

In the 5th synthetic route, a high temperature is necessary for the thermal dissociation and the yield of 6% is very low.

In the 6th method of synthesis, which describes only the preparation of 1-methyl-5-hydroxypyrazole, use is made of 3-alkoxyacrylic esters which are cumbersome to prepare and expensive. 3-alkoxyacrylic esters are prepared by reaction of methanol with expensive propiolic esters (Tetrahedron Lett. 1983, 24, 5209, J. Org. Chem. 1980, 45, 48, Chem. Ber. 1966, 99, 450, Chem. Lett. 1996, 9, 727–728), by reaction of expensive and difficult-to-synthesize α,α-dichloro (diethyl ether) with bromoacetic esters (Zh. Org. Khim. 1986, 22, 738), by reaction of bromoacetic esters with trialkyl formates (Bull. Soc. Chim. France 1983, N 1–2, 41–45) and by elimination of methanol from 3,3-dialkoxypropionic esters (DE 3701113) (obtainable by reaction of the expensive methyl propiolate with methanol (J. Org. Chem. 1976, 41, 3765), by reaction of 3-N-acetyl-N-alkyl-3-methoxypropionic esters with methanol (J. Org. Chem. 1985, 50, 4157–4160, JP 60-156643), by reaction of acrylic esters with alkylamines and acetic anhydride (J. Org. Chem. 1985, 50, 4157–4160), by reaction of ketene with trialkyl orthoformate (DK 158462), by palladium—and simultaneously copper-catalyzed reaction of acrylic esters with methanol (DE 4100178.8), by reaction of trichloroacetyl chloride with vinyl ethyl ether (Synthesis 1988, 4, 274), by reaction of α,α,α-trichloro-B-methoxybuten-2-one with methanol (Synthesis 1988,4, 274) and by reaction of the sodium salts of 3-hydroxyacrylic esters with alcohols (DE 3641605)). The poor accessibility of the 3-alkoxyacrylic esters therefore makes the synthesis by the 6th route uneconomical. Furthermore, JP 189 271/86 describes the isolation of 5-hydroxy-1-methylpyrazole as hydrochloride but gives no information on the isolation and purification of the free base. If an attempt is made to employ the reaction conditions described in JP 189 271/86 and to isolate the free base, only very small yields which are uneconomical for an industrial-scale preparation of hydroxypyrazoles are obtained.

Consequently, these synthetic routes cannot be considered to be economical and efficient processes for preparing 1-alkyl-5-hydroxypyrazoles. This applies particularly to the industrial preparation of 1-alkyl-5-hydroxypyrazoles in large quantities.

It is an object of the present invention to provide an alternative process for preparing 1-alkyl-5-hydroxypyrazoles which does not have the abovementioned disadvantages of the previously known preparative methods.

We have found that this object is achieved by the process of the present invention.

The present invention provides a process for preparing compounds of the formula I

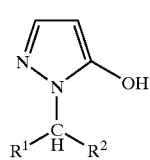

I in which $R^1$ is hydrogen, an aliphatic group having 1–8 carbon atoms, $C_1$–$C_6$-alkoxycarbonyl, $C_1$–$C_6$- alkylthiocarbonyl or a cyclic ring system having 3–14 ring atoms, and $R^2$ is hydrogen, an aliphatic group having 1–8 carbon atoms, or $R^1$ and $R^2$ together with the carbon atom to which they are bound form a cyclic or bicyclic ring system having 3–14 ring atoms, comprising the preparation of compounds of the formula II

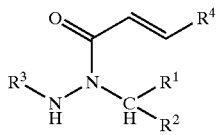

II in which $R^3$ and $R^4$ are readily detachable groups and $R^1$ and $R^2$ are as defined above, as starting materials or intermediates and cyclization of these under suitable reaction conditions to give compounds of the formula I.

The process of the present invention makes it possible to prepare compounds of the formula I in a high yield. The cyclization proceeds in yields of at least 80%, in the case of less bulky radicals R at least 90%. Less bulky radicals are, in particular, those in which the group —$CHR^1R^2$ is a group having 1–6 carbon atoms. Another advantage is that diacylhydrazines of the formula II can be converted into the 1-substituted 5-hydroxypyrazoles of the formula I under particularly convenient conditions, for example short reaction times. The cyclization is preferably catalyzed by acids or bases. A further advantage is that the starting compounds required for the synthesis are readily available and inexpensive. Additional advantages are that the compounds of the formula II are obtained in high purity and that the hydroxypyrazoles of the formula I can be obtained in free form, i.e. essentially free of acid addition salts. In the previously known syntheses, the hydroxypyrazoles were virtually always formed as their acid addition salts, e.g. hydrochlorides, which had to be converted into the free hydroxypyrazoles in an additional work-up step. In the synthesis according to the present invention, on the other hand, the hydroxypyrazoles are obtained directly in the form of the free base which is essentially free of acid addition salts. A further advantage of the process of the present invention is that the 3-hydroxypyrazoles are obtained regioselectively. The proportion of 3-hydroxypyrazoles is low. The yield of 5-hydroxypyrazoles in the synthesis according to the present invention is therefore higher than in the known methods of preparation. Owing to the relatively small amounts in which by-products such as 5-hydroxypyrazoles are formed, a more economical process for preparing the 5-hydroxypyrazoles can thus be carried out.

The diacylhydrazines of the formula II are prepared, for example, by reacting compounds of the formula III

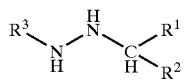

III with activated alkenylcarboxylic acid derivatives of the formula 10 IV

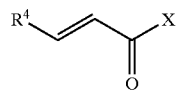

IV where $R^3$ and $R^4$ are readily detachable groups and X is a suitable leaving group, with elimination of HX and subsequent isolation of compounds of the formula II:

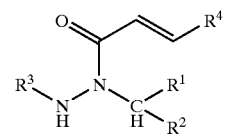

II

For the reaction of III with IV, it is advantageous to use MTBE as solvent and triethylamine as base.

Compounds of the formula III are obtained, for example, by reaction of compounds of the formula V

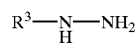

V with compounds of the formula VI

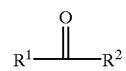

VI and subsequent catalytic hydrogenation of the intermediate N-acylhydrazones of the formula VII

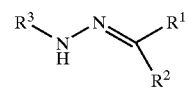

VII to give the compounds of the formula III. As catalysts in the catalytic hydrogenation, use is made of Raney-nickel, Pd, Pt or Adams catalysts.

The resulting compounds of the formula III can either be isolated and subsequently reacted with the activated alkenylcarboxylic acid derivatives of the formula IV or be advantageously reacted directly in the reaction solution with the compounds of the formula IV. In the latter case, purification of the intermediates III can be omitted. The reaction conditions for the hydrogenation are described in more detail in the literature, e.g. when using $H_2$/nickel catalysts: DE 1003215; $H_2$/Ray-Ni: OD 84-007127/02; using $H_2$/$PtO_2$: Acta. Chem. Scand. 1967, 21, 2363–2366; using $H_2$/Pt: Ann. Chimica 1968, 58, 1336–1353; using $H_2$/Pd: Indian J. Chem. 1964, 10, 423–424.)

The cyclization of compounds of the formula II is carried out in the presence of acid or base catalysts, with the group $R^3$ on the terminal nitrogen atom and the group $R^4$ being eliminated at the same time. The cyclization is preferably carried out using mineral acids such as hydrochloric acid or sulfuric acid.

The process of the present invention for preparing compounds of the formula I can be summarized by means of the following reaction scheme, where, for example, $R^1$ is an alkyl group, $R^2$ is hydrogen, $R^3$ is the group $H_3C$—CO— and $R^4$ is an alkoxy group:

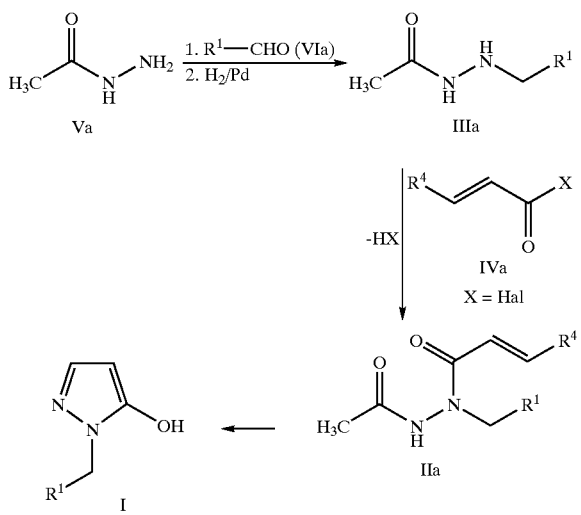

The yield in the addition of ketones or aldehydes of the formula VI onto hydrazines of the formula V and the subsequent hydrogenation is in each case at least 80%, frequently in the range from 85 to 90%. The acylation of compounds of the formula III to form compounds of the formula II proceeds in a yield of at least 80%, in the above case in the range from 80 to 90%.

In the definition of the various radicals in the formulae, the terms employed, either on their own (e.g. "$C_1$–$C_6$-alkyl") or as parts of or in combination with other chemical groups (e.g. halo-"$C_1$–$C_6$-alkyl", etc.), essentially serve as a collective term for a group of compounds. If some of the abovementioned radicals bear one or more substituents, the substituents can in principle be identical or different. Specific meanings of the terms used are:

Aliphatic groups: straight-chain or branched alkyl, alkenyl or alkynyl having in each case up to 8 carbon atoms, where these groups may be substituted by one or more halogen atoms, halo-$C_1$–$C_6$-alkyl groups, $C_1$–$C_6$-alkoxy or aryloxy. Aryloxy is preferably the phenoxy or benzyloxy group.

Alkyl: straight-chain or branched alkyl groups having 1–6, preferably 1–4 carbon atoms, for example the following groups: methyl, ethyl, propyl, 1-methylethyl, butyl, 1-methylpropyl, 2-methylpropyl and 1,1-dimethylethyl; pentyl, 1-methylbutyl, 2-methylbutyl, 3-methylbutyl, 2,2-dimethylpropyl, 1 -ethylpropyl, hexyl, 1,1-dimethylpropyl, 1,2-methylpropyl, 1-methylpentyl, 2-methylpentyl, 37methylpentyl, 4-nethylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl.

Alkenyl: straight-chain or branched alkenyl groups having 2–6, preferably 2–4 carbon atoms, for example the following groups: ethylene, prop-l-en-1-yl, prop2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl and 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2n-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethyl-prop-1-en-1-yl, 1,2-dimethylprop-2-en-1-yl, 1-ethylprop-1-en-2-yl, 1-ethylprop-2-en-1-yl, hex-len-1-yl, hex-2-en-1-yl, hex-3-en-1-yl, hex-4-en-1-yl, hex-5-en-1-yl, 1-methylpent-l-en-1-yl, 2-methylpent-l-en-1-yl, 3-methylpent-l-en-1-yl, 4-methylpent-1-en-1-yl, 1-methylpent-2en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimetylbut-l-en-1-yl, 1,3-dimethylbut-2-en-1-yl, 1,3-dimethylbut-3-en-1-yl, 2,2-dimethylbut-3-en-1-yl, 2,3-dimetylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl.

Alkynyl: straight-chain or branched alkynyl groups having 2–6, preferably 2–4, carbon atoms, for example the following groups: ethynyl, prop-1-yn-1-yl, prop-2-yn-1-yl, 1-methylethynyl, butyn-1-yl, butyn-2-yl, butyn-3-yl, 1-methylprop-1-yn-1-yl, 2-methylprop-1-yn-1-yl, 1-methylprop-2-yn-1-yl and 2-methylprop-2-yn-1-yl, pentyn-1-yl, pentyn-2-yl, pentyn-3-yl, pentyn-4-yl, 1-methylbut-1-yn-1-yl, 2-methylbut-1-yn-1-yl, 3-methylbut-1-yn-1-yl, 1-methylbut-2-yn-1-yl.

Alkoxy: straight-chain or branched alkoxy groups having 1–6, preferably 2–4, carbon atoms, for example methoxy, ethoxy, isopropyloxy, 2-methylbut-1-yloxy.

Haloalkyl: alkyl groups as mentioned above which are substituted by from 1 to 3 halogen atoms, for example trifluoromethyl, difluoromethyl, dichloromethyl, 1,1-dichloroethyl, 1,2-dichloroethyl.

Halogen: fluorine, chlorine, bromine or iodine, preferably fluorine or chlorine.

Cyclic ring system: a monocyclic ring system having 3–14, preferably 3–8, ring atoms, where the ring atoms can be carbon, nitrogen or sulfur. Carbocyclic ring systems preferably have 3–8 carbon atoms, e.g. cyclopropyl, cyclobutyl, cyclopentyl, cyclohexyl, cycloheptyl or cyclooctyl. The cyclic ring systems can also have one or more double bonds ($C_3$–$C_8$-cycloalkenyl groups). Aromatic ring systems are, in particular, phenyl and naphthyl. If the cyclic ring systems are heterocyclic ring systems, one, two or three carbon atoms can be replaced by heteroatoms, e.g. O, N, S. In principle, the cyclic ring systems can be aromatic, partially hydrogenated or fully hydrogenated. The cyclic ring systems can also be substituted in any way. Examples of suitable substituents are the following groups: $C_1$–$C_6$-alkyl, halogen, halo-$C_1$–C6-alkyl, amino, hydroxy, oxo, $C_1$–$C_6$-alkylamino, di-$C_1$–$C_6$-alkylamino, sulfhydryl, sulfonyl, $C_1$–$C_6$-alkylsulfonyl, etc.

Bicyclic ring system: a bicyclic ring system having 7–14 ring atoms, preferably 7–10 ring atoms, where the ring atoms may be carbon and one or two nitrogen atoms. The ring systems can also have one or two double bonds. In principle, the ring systems can be monosubstituted or polysubstituted by alkyl, alkoxy, hydroxy, oxo or halogen. Examples are: adamantyl, camphyl, camphenyl, norbornyl.

If $R^1$ and $R^2$ together with the carbon atom to which they are bound form a cyclic ring system, this is one of the abovementioned cyclic systems,, preferably $C_3$–$C_8$-cycloalkyl groups such as the following: cyclopropyl, cyclobutyl, cyclopentyl, cyclohexyl, cycloheptyl or cyclooctyl, and also their unsaturated derivatives having one, two or three double bonds in the ring system.

If $R^1$ is a cyclic ring system having 3–14 ring atoms, it is preferably one of the following groups: $C_3$–$C_{14}$-cycloalkyl, $C_3$–$C_{14}$-cycloalkenyl, aromatic groups such as phenyl, naphthyl, and also their partially hydrogenated derivatives.

If the aliphatic radical, in particular an alkyl group, is substituted, preference is given to the following substituents: halogen, $C_1$–$C_6$-alkyl, $C_1$–$C_6$-alkoxycarbonyl. The aliphatic radical can be monosubstituted or polysubstituted. In this context, $R^1$ is preferably: difluoromethyl, trifluoromethyl, ethoxycarbonyl, 1,1-diethoxymethylene, 1,1-dimethoxymethylene.

$R^2$ is preferably a hydrogen atom.

$R^3$ is a group which can be readily detached under acidic or basic conditions or thermally, for example alkylcarbonyl, in particular acetyl, propionyl, butyryl, preferably acetyl.

$R^4$ is likewise a group which can readily be detached under acidic or basic conditions or thermally, for example alkoxy, in particular 2-methylprop-1-yloxy (—O—$CH_2$-CH($CH_3$)$_2$)

The present invention also provides novel compounds of the formula I which are essentially free of acid addition salts. It also provides compounds of the formula I in which $R^1$ is preferably $C_4$–$C_6$-alkyl, halo-$C_1$–$C_6$-alkyl, $C_1$–$C_6$-alkoxycarbonyl or $C_1$–$C_6$-alkylthiocarbonyl. These compounds are valuable starting materials for preparing further chemical compounds containing a hydroxypyrazole radical, for example compounds having a herbicidal action, as already mentioned at the outset.

The process of the present invention is particularly suitable for the preparation of compounds of the formula I in which the following radicals, either alone or in each case in combination with one another, have the following meanings:

1. $R^1$ and $R^2$ together form a bicyclic ring system, especially adamantyl, norbornyl, camphyl.
3. $R^1$: hydrogen; alkyl; alkyl which is monosubstituted or disubstituted by alkoxy; phenyl; haloalkyl; alkoxycarbonyl. In this context, $R^1$ is preferably: methyl, ethyl, n-propyl, i-propyl; diethoxymethyl, 2,2-diethoxyeth-1-yl; trifluoromethyl; methoxycarbonyl, ethoxycarbonyl.
4. $R^2$: hydrogen, alkyl.

The present invention additionally provides novel compounds of the formula II (diacylhydrazines) which can be used as intermediates. Here, the group —$CHR^1R^2$ has the abovementioned meanings. $R^1$ is, in particular, hydrogen, an aliphatic group having 1–8 carbon atoms, $C_1$–$C_6$-alkoxycarbonyl, $C_1$–$C_6$-alkylthiocarbonyl or a cyclic ring system having 3–14 ring atoms. $R^2$ is in particular hydrogen. $R^1$ and $R^2$ may also, according to the present invention, together form a cycloalkyl group or a bicyclic ring system in the above-defined sense.

The following table shows novel intermediates of the formula II which can be prepared by the methods described in the examples:

TABLE 1

Compounds of the formula II

II.A

| No. II.A | $R^1$ | $R^2$ | $R^1$ and $R^2$ |
|---|---|---|---|
| 1. | H | $CH_3$ | |
| 2. | H | $C_2H_5$ | |
| 3. | H | n-$C_3H_7$ | |
| 4. | H | i-$C_3H_7$ | |
| 5. | H | n-$C_4H_9$ | |
| 6. | H | sec-$C_4H_9$ | |
| 7. | H | tert-$C_4H_9$ | |
| 8. | H | $CH_2$-phenyl | |
| 9. | H | $CF_3$ | |
| 10. | H | CO—$OC_2H_5$ | |
| 11. | H | $CH(OC_2H_5)_2$ | |
| 12. | H | $CH_2$—$CH(OC_2H_5)_2$ | |
| 13. | $CH_3$ | $CH_3$ | |
| 14. | $CH_3$ | $C_2H_5$ | |
| 15. | $CH_3$ | n-$C_3H_7$ | |
| 16. | $CH_3$ | i-$C_3H_7$ | |
| 17. | $CH_3$ | n-$C_4H_9$ | |
| 18. | $CH_3$ | sec-$C_4H_9$ | |
| 19. | $CH_3$ | tert-$C_4H_9$ | |
| 20. | $CH_3$ | $CH_2$-phenyl | |
| 21. | $CH_3$ | $CF_3$ | |
| 22. | $CH_3$ | CO—$OC_2H_5$ | |
| 23. | $CH_3$ | $CH(OC_2H_5)_2$ | |
| 24. | $CH_3$ | $CH_2$—$CH(OC_2H_5)_2$ | |
| 25. | — | — | cyclopropyl |
| 26. | — | — | cyclobutyl |
| 27. | — | — | cyclopentyl |
| 28. | — | — | cyclohexyl |
| 29. | — | — | cycloheptyl |
| 30. | — | — | cyclooctyl |
| 31. | — | — | 2-adamantyl |
| 32. | — | — | 2-norbornyl |
| 33. | — | — | camphyl |

The invention also provides compounds of the formula III (hydrazines) which can be used as intermediates. Here, the group —$CHR^1R^2$ is as defined above. $R^1$ is, in particular, hydrogen, an aliphatic group having 1–8 carbon atoms which may bear one or more halogen atoms or $C_1$–$C_6$-alkoxy groups as substituents, $C_1$–$C_6$-alkoxycarbonyl, $C_1$–$C_6$-alkylthiocarbonyl or a cyclic ring system having 3–14 ring atoms. In particular, $R^1$ is trifluoromethyl, methoxycarbonyl, ethoxycarbonyl, dimethoxymethyl, diethoxymethyl, 2,2-dimethoxyethyl or 2,2-diethoxyethyl.

The following table shows novel intermediates of the formula III which can be prepared by methods analogous to those described in the examples:

TABLE 2

Compounds of the formula III

IIIa

| No. III.a | $R^1$ | $R^2$ | $R^1$ and $R^2$ |
|---|---|---|---|
| 1. | H | $CF_3$ | — |
| 2. | H | CO—$OC_2H_5$ | — |

TABLE 2-continued

Compounds of the formula III

IIIa $$H_3C-\underset{\underset{H}{\|}}{C}-\underset{H}{N}-\underset{H}{N}-\underset{H}{C}\begin{matrix}R^1\\R^2\end{matrix}$$

| No. III.a | R$^1$ | R$^2$ | R$^1$ and R$^2$ |
|---|---|---|---|
| 3. | H | CH(OC$_2$H$_5$)$_2$ | — |
| 4. | H | CH$_2$—CH(OC$_2$H$_5$)$_2$ | — |
| 5. | CH$_3$ | CH$_3$ | — |
| 6. | H | cyclopentyl | — |
| 7. | — | — | 2-adamantyl |
| 8. | — | — | 2-norbornyl |
| 9. | — | — | 2-camphyl |

The process of the present invention is illustrated by the following examples:

EXAMPLE 1

Preparation of 1-ethyl-5-hydroxypyrazole a) N-acyl-N'-ethylhydrazine 192 g of N-acyl-N'-ethylhydrazone together with 1.4 l of methanol and 40 g of Raney nickel are placed in a hydrogenation autoclave. Hydrogenation is carried out at from 20 to 110° C. and from 4 to 40 bar hydrogen pressure until no more hydrogen is taken up. After the hydrogenation is complete, the catalyst is separated off and the solvent is removed under reduced pressure. This gives 190 g (95%) of N-acyl-N'-ethylhydrazine.

b) Reaction of N-acyl-N'-ethylhydrazine with isobutoxyacryloyl chloride 230 g of N-acyl-N'-ethylhydrazine and 194 g of triethylamine are suspended in 950 g of tert-butyl methyl ether. A total of 282 g of acid chloride is added dropwise, 630 g of water are subsequently added and the mixture is stirred for a further period. The phases are separated, the organic phase is dried and the solvent is removed. This gives 348 g (99%) of the unsymmetrical diacylhydrazine.

1H-NMR (d6-DMSO): 6=0.9 (6 H), 1.0 (3 H), 1.9 (3 H), 3.5 (2 H), 3.6 (2 H), 5.6 (1 H), 7.3 (1 H), 10 (1 H).

c) 1-ethyl-5-hydroxypyrazole 348 g of unsymmetrical diacylhydrazine together with 2000 g of 10% strength sulfuric acid are placed in a reaction vessel and heated to 90° C. After one hour, the mixture is cooled to room temperature and the pH is set to 4 using sodium hydroxide. The mixture is evaporated and the residue is distilled. This gives 164 g (97%) of 1-ethyl-5-hydroxypyrazole.

EXAMPLE 2

Preparation of 1-benzyl-5-hydroxypyrazole a) N-acyl-N'benzylhydrazine 50 g of hydrazine hydrate are added dropwise to 115.5 g of boiling methyl acetate and the mixture is subsequently stirred for another 1.5 hours under reflux. It is then cooled to 17° C. and 200 ml of methanol followed by 106 g of benzaldehyde are subsequently added. Stirring for another 35 minutes at room temperature and subsequent evaporation gives 199 g of the imino compound which is reacted directly without further purification.

66.3 g of the imino compound prepared above are hydrogenated in the presence of 6 g of Raney nickel in 120 ml of methanol for 12 hours at 90° C. at a pressure of 100 bar of hydrogen in an autoclave. The residue is filtered and the solvent is removed, giving 48.4 g of the hydrogenation product.

b) Reaction of N-acyl-N'-benzylhydrazine with isobutoxyacryloyl chloride 37.6 g of N-acyl-N'-benzylhydrazine in 190 ml of methyl acetate are placed in a reaction vessel and 35.8 g of sodium acetate are added. At 11° C., 39 g of acid chloride are added and the mixture is subsequently admixed with 80 ml of water. The phases are separated and 79.3 g of desired product are obtained after evaporation.

c) 1-Benzyl-5-hydroxypyrazole 79.2 g of unsymmetrical diacylhydrazine and 70 g of 50% strength sulfuric acid are placed in a reaction vessel. The mixture is stirred at 85–90° C. for 35 minutes and the pH is subsequently set to 4.9 using 136 g of 23% strength NaOH solution in methanol. After filtration, the filtrate is evaporated and the residue is recrystallized from ethyl acetate. This gives 35 g of 1-benzyl-5-hydroxypyrazole.

EXAMPLE 3

Using a procedure similar to that in the above-described examples, the following compounds were prepared:

| Ex. No. | Structure | physical and NMR data |
|---|---|---|
| 3.1 | pyrazole-OH, N-Me | 1H-NMR (d6-DMSO): 3.5 (s, 3H), 5.2 (d, 1H), 7.1 (d, 1H), 9.5 (br., 1H). |
| 3.2 | pyrazole-OH, N-Et | mp. 94° C. 1H-NMR (d6-DMSO): 1.3 (t, 3H), 3.9 (q, 2H), 5.3 (d, 1H), 7.3 (d, 1H), 10.4 (br., 1H). |
| 3.3 | pyrazole-OH, N-nPr | bp. (1 mbar): 114° C. 1H-NMR (d6-DMSO): 0.8 (t, 3H), 1.6 (m, 2H), 3.7 (t, 2H), 5.3 (d, 1H), 7.0 (d, 1H). |
| 3.4 | pyrazole-OH, N-nBu | bp. (0.5 mbar): 107–108° C. 1H-NMR (d6-DMSO): 0.9 (t, 3H), 1.2 (m, 2H), 1.7 (m, 2H), 3.8 (t, 2H), 5.2 (d, 1H), 7.0 (d, 1H), 9.1 (br., 1H). |
| 3.5 | pyrazole-OH, N-iBu | bp. (2 mbar): 135° C. 1H-NMR (d6-DMSO): 0.9 (d, 6 H), 2.1 (sept., 1H), 3.5 (d, 2H), 5.2 (d, 1H), 7.0 (d, 1H), 10.6 (br., 1H). |
| 3.6 | pyrazole-OH, N-CH$_2$Ph | 1H-NMR (d6-DMSO): 5.1 (s, 2H), 5.3 (s, 1H), 7.1–7.3 (m, 6H), 11.1 (br., 1H). |

| Ex. No. | Structure | physical and NMR data |
|---|---|---|
| 3.7 | pyrazole with N-CH2-CF3 and OH | 1H-NMR (d6-DMSO): 4.7 (q, 2H), 5.4 (d, 1H), 7.3 (d, 1H), 11.4 (br., 1H). |
| 3.8 | pyrazole with N-CH2-C(O)-OEt and OH | 1H-NMR (d6-DMSO): 1.2 (t, 2H), 4.1 (q, 2H), 4.7 (s, 2H), 5.3 (d, 1H), 7.2 (d, 1H), 11.2 (br., 1H). |
| 3.9 | pyrazole with N-CH2-CH(OEt)2 and OH | 1H-NMR (d6-DMSO): 1.0 (t, 6H), 3.3 (m, 2H), 3.6 (m, 2H), 3.9 (d, 2H), 4.7 (t, 1H), 5.3 (d, 1H), 7.1 (d, 1H), 11.0 (br., 1H). |
| 3.10 | pyrazole with N-CH2CH2CH(OEt)2 and OH | 1H-NMR (d6-DMSO): 1.1 (t, 6H), 1.9 (m, 2H), 3.4 (m, 2H), 3.6 (m, 2H), 3.9 (m, 2H), 4.5 (m, 1H), 5.3 (d, 1H), 7.1 (d, 1H), 11.0 (br., 1H). |
| 3.11 | pyrazole with N-isopropyl and OH | 1H-NMR (d6-DMSO): d=1.3 (d, 6H), 4.3 (sept., 1H), 5.2 (d, 1H), 7.1 (d, 1H), 11 (br, 1H). |

EXAMPLE 4

Preparation of 1-isopropyl-5-hydroxypyrazole a) N-isopropyl-N'-acetylhydrazide (Compound of the type III with R³=H₃CCO; —CHR¹R² =isopropyl) 56.2 g (0.76 mol) of acetylhydrazide (1), 51.2 g (0.88 mol) of acetone, 200 ml of methanol and 24 g of Raney nickel are stirred at room temperature for 3 hours and the mixture is subsequently stirred for 2 hours at 80° C. and a hydrogen pressure of 100 bar. The solid is filtered off with suction, the filtrate is evaporated and the residue is distilled (0.2.bar, bp. 108–113° C.). This gives 299 g (85%) of the title compound.

b) N-isopropyl-N-(3-butoxyacrylamido)-N'-acetylhydrazide (Compound of the type II with R³=H₃CCO; —CHRIR² =isopropyl; R⁴=—O-CH₂-CH (CH₃)₂)

299 g (2.59 mol) of the compound obtained in a) and 425 g of sodium acetate together with 1.2 l of methyl acetate are placed in a reaction vessel and 390 g (2.4 mol) of 3-butoxyacryloyl chloride are added dropwise and the mixture is stirred for another 10 minutes for a further 31 g (0.19 mol) of 3-butoxyacryloyl chloride to be added dropwise. After 15 minutes, 900 ml of water are added and the phases are separated. The solvent is taken off on a rotary evaporator and the residue is distilled (0.4 mbar, going over at 120° C.).

Yield: 565 g (90%) of the title compound.

c) 1-isopropyl-5-hydroxypyrazole

While cooling, 563 g (2.32 mol) of the compound obtained in b) are added to 497 g of conc. HCl and the mixture is stirred at room temperature. The pH is set to 4.4 using 50% strength NaOH and the mixture is evaporated. Methanol is subsequently added, the mixture is filtered with suction, the solvent is removed from the filtrate and the residue is distilled (0.3 bar, bp. 153° C.); the product is then recrystallized from ethyl acetate. Mp. 117–118° C. Yield: 264 g (90%) of the title compound. 1H-NMR (d6-DMSO): ε=1.3 (d, 6 H), 4.3 (sept., 1 H), 5.2 (d, 1 H), 7.1 (d, 1 H), 11 (br, 1 H).

We claim:

1. A diacylhydrazine of the formula II

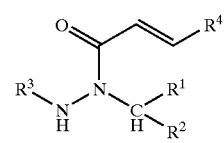

II where

R¹ is hydrogen, straight-chain or branched alkyl, alkenyl or alkynyl having in each case 1 to 8 carbon atoms, where these groups may be substituted by one or more halogen atoms, halogen —C₁–C6-alkyl groups, C₁–C₆-alkoxy or aryloxy, C₁–C₆-alkoxycarbonyl, C₁–C₆-alkylthiocarbonyl or a cyclic ring system having 3 to 14 ring atoms, and R² is hydrogen, straight-chain or branched alkyl, alkenyl or alkynyl, having in each case 1 to 8 carbon atoms, where these groups may be substituted by one or more halogen atoms, halogen —C₁–C₆-alkyl groups, C₁–C6-alkoxy or aryloxy, R¹ and R² together with the carbon atom to which they are bound form a cyclic ring system having 3 to 14 ring atoms or a bicyclic ring system having 7 to 14 ring atoms, R³ is C₁–C₆-alkylcarbonyl, and R⁴ is C₁–C₄-alkoxy.

2. The diacylhydrazine as claimed in claim 1 wherein the group —CHR¹R² is a bicyclic ring system selected from the group consisting of adamantyl, norbornyl and camphyl.

3. The diacylhydrazine as claimed in claim 1 wherein the group —CHR¹R² is C₃–C₈-cycloalkyl.

4. The diacylhydrazine as claimed in claim 1 wherein R¹ is a hydrogen atom.

5. The diacylhydrazine as claimed in claim 1 wherein R² is a C₁–C₆-alkyl group.

6. The diacylhydrazine as claimed in claim 1 wherein R³ is acetyl and R⁴ is 2-methyl-1-propyloxy.

7. A process for preparing a diacylhydrazine of the formula II

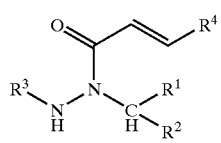

where

R[1] is hydrogen, 6straight-chain or branched alkyl, alkenyl or alkynyl having in each case 1 to 8 carbon atoms, where these groups may be substituted by one or more halogen atoms, halogen —$C_1$–$C_6$-alkyl groups, $C_1$–$C_6$-alkoxy or aryloxy, $C_1$–$C_6$-alkoxycarbonyl, $C_1$–$C_6$-alkylthiocarbonyl or a cyclic ring system having 3 to 14 ring atoms, and R[2] is hydrogen, straight-chain or branched alkyl, alkenyl or alkynyl, having in each case 1 to 8 carbon atoms, where these groups may be substituted by one or more halogen atoms, halogen —$C_1$–$C_6$-alkyl groups, $C_1$–$C_6$-alkoxy or aryloxy, R[1] and R[2] together with the carbon atom to which they are bound form a cyclic ring system having 3 to 14 ring atoms or a bicyclic ring system having 7 to 14 ring atoms, R[3] is $C_1$–$C_6$-alkylcarbonyl, and R[4] is $C_1$–$C_4$-alkoxy, said process comprising:

i the preparation of a compound of the formula III,

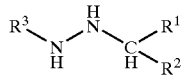

in which R[1], R[2] and R[3] are as defined above, by reacting a compound of the formula V

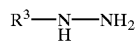

with a compound of the formula VI

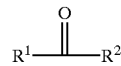

and subsequently hydrogenating the resulting compound of the formula VII

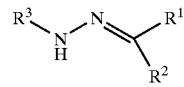

to form a compound of the formula III, ii reacting the compound of the formula III with an activated alkenylcarboxylic acid derivative of the formula IV

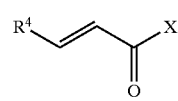

in which R[4] is as defined above and X is a suitable leaving group, to form a compound of the formula II.

8. The process as claimed in claim 7 wherein the reaction of compounds of the formula III with compounds of the formula IV is carried out at from −10° C. to 100° C.

9. The process as claimed in claim 8 wherein the reaction is carried out at from 10° to 30° C.

10. The process as claimed in claim 7 wherein the reaction of compounds of the formula III with compounds of the formula IV is carried out in an ether as solvent.

11. The process as claimed in claim 10 wherein the ether is selected from THF, MTBE or 1,2-dimethoxyethane or a mixture thereof.

12. The process as claimed in claim 1 wherein the reaction of compounds of the formula III with compounds of the formula IV is carried out in the presence of a HX trap, which is selected from alkali metal salts of carboxylic acids, alkaline earth metal salts of carboxylic acids and compounds of the formula III.

* * * * *

UNITED STATES PATENT AND TRADEMARK OFFICE
CERTIFICATE OF CORRECTION

PATENT NO.    : 6,600,071 B2
DATED         : July 29, 2003
INVENTOR(S)   : Goetz et al.

It is certified that error appears in the above-identified patent and that said Letters Patent is hereby corrected as shown below:

<u>Title page,</u>
Item [57], ABSTRACT,
Line 2 after formula I, "$C_{l}$-$C_6$-alkoxycarbonyl, $C_{l}$-$C_6$-" should be -- $C_1$-$C_6$-alkoxycarbonyl, $C_1$-$C_6$- --.

<u>Column 12,</u>
Line 36, "halogen-$C_1$-C6-alkyl" should be -- halogen-$C_1$-$C_6$-alkyl --;
Line 44, "$C_1$-C6-" should be -- $C_1$-$C_6$- --.

<u>Column 13,</u>
Line 11, "6straight-chain" should be -- straight-chain --;
Line 32, "i the" should be -- i. the --.

<u>Column 14,</u>
Line 17, "ii reacting" should be -- ii. reacting --.

Signed and Sealed this

Sixteenth Day of September, 2003

JAMES E. ROGAN
*Director of the United States Patent and Trademark Office*